United States Patent [19]  [11]  4,429,118
Durette  [45]  Jan. 31, 1984

[54] METHYL 3-AZIDO-4-C-CYANO-2,3,4,6-TETRADEOXY-α-D-ARABINO-HEXOPYRANOSIDE AND PROCESSES FOR ITS PREPARATION

[75] Inventor: Philippe L. Durette, New Providence, N.J.

[73] Assignee: Merck & Co., Inc., Rahway, N.J.

[21] Appl. No.: 374,574

[22] Filed: May 3, 1982

Related U.S. Application Data

[62] Division of Ser. No. 248,178, Mar. 30, 1981, Pat. No. 4,348,325.

[51] Int. Cl.$^3$ ............................................. C07H 15/04
[52] U.S. Cl. ...................................... 536/17.2; 536/18.4
[58] Field of Search ...................... 536/17.2, 18.4, 122, 536/118; 549/419

[56] References Cited

U.S. PATENT DOCUMENTS 3,632,804  1/1972  Gray et al. ........................... 536/118
4,234,596  11/1980  Christensen et al. ............... 424/274
4,348,325  7/1982  Durette ................................ 549/419

*Primary Examiner*—Johnnie R. Brown
*Attorney, Agent, or Firm*—Daniel T. Szura; Hesna J. Pfeiffer

[57] ABSTRACT

Disclosed is methyl 3-azido-4-C-cyano-2,3,4,6-tetradeoxy-α-D-arabino-hexopyranoside and processes for its preparation from methyl 3-azido-2,3,6-trideoxy-α-D-arabino-hexopyranoside via the 4-bromo-4-deoxy intermediate; wherein the two inversions of configuration at C-4 result in a net retention of the α-D-arabino stereochemistry.

2 Claims, No Drawings

METHYL 3-AZIDO-4-C-CYANO-2,3,4,6-TETRADEOXY-α-D-ARABINO-HEXOPYRANOSIDE AND PROCESSES FOR ITS PREPARATION

This is a division of application Ser. No. 248,178, filed Mar. 30, 1981, U.S. Pat. No. 4,348,325.

BACKGROUND OF THE INVENTION

This invention relates to the compound methyl 3-azido-4-C-cyano-2,3,4,6-tetradeoxy-α-D-arabino-hexopyranoside (VI) and its utility in the synthesis of the known antibiotic (+)-thienamycin (I).

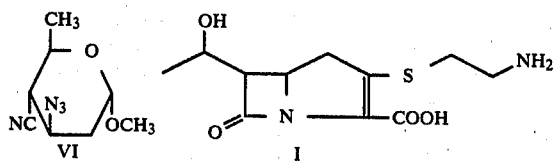

This invention also relates to processes for preparing VI from methyl 3-azido-2,3,6-trideoxy-α-D-arabino-hexopyranoside (IV). The following scheme is representative of such processes:

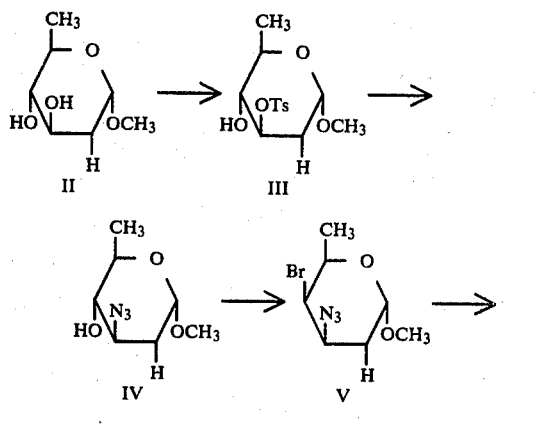

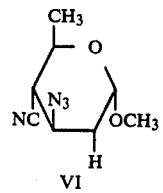

As described below, the process proceeding from starting material II, via the intermediate 3-azido-3-deoxy sugar IV and 4-bromo-4-deoxy sugar V, performs a regioselective p-toluenesulfonylation of the C-3 hydroxyl of starting material II to give tosylate III; a replacement of the C-3 tosylate with an azido function with retention of configuration at C-3 to afford IV; and two inversions of configuration at C-4 of IV with a net retention of the α-D-arabino stereochemistry in VI.

The utility of the resulting compound VI in the chiral total synthesis of thienamycin is described in copending, commonly assigned, concurrently filed U.S. patent application Ser. Nos. 248,177, now U.S. Pat. No. 4,384,998; 248,176, now U.S. Pat. No. 4,324,900; and 248,174; which are incorporated herein by reference to the extent that they describe the utility of compound VI. Also incorporated by reference is U.S. patent application Ser. No. 112,058 filed Jan. 14, 1980, now abandoned, which describes the total synthesis of thienamycin and which proceeds from an intermediate species which is common to the instant disclosure and as described in the three previously mentioned, concurrently filed U.S. patent applications. Also incorporated by reference are U.S. Pat. No. 4,234,596 (issued Nov. 18, 1980), and EPO Application No. 79,101,307-1 (publication No. 0007973 filed May 1, 1979), which publications disclose schemes of total synthesis which can be fed by common intermediates made available by the presently disclosed and claimed processes.

DETAILED DESCRIPTION OF THE INVENTION

The process of the present invention may conveniently be represented by the following reaction diagram:

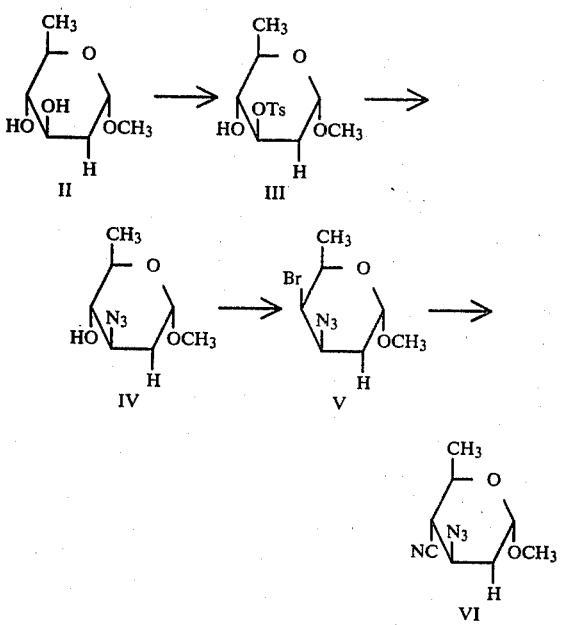

In words relative to the above reaction sequence, the known starting methyl 2,6-dideoxy-α-D-arabinohexopyranoside (II), in a solvent such as pyridine or dichloromethane, chloroform or the like is treated with p-toluenesulfonyl chloride, p-toluenesulfonic anhydride, or the like in the presence of a base such as Et₃N, iPr₂NEt, pyridine, 4-dimethylaminopyridine, or the like, at a temperature of from −15° C. to 10° C. from 24 hours to 10 days to yield the resulting C-3 tosylate III, which upon treatment, in a solvent such as ethanol, methanol, or the like, with alcoholic base, such as ethanolic sodium hydroxide, ethanolic potassium hydroxide, methanolic sodium hydroxide, methanolic potassium hydroxide, or the like, followed by treatment with an alkali azide, such as lithium azide, sodium azide, potassium azide, or the like in the presence of ammonium chloride at a temperature of from 50° C. to 100° C. from 1 hour to 24 hours yields the azide IV.

Treatment of IV in a solvent such as dichloromethane, chloroform, or the like with trifluoromethanesulfonyl chloride, trifluoromethanesulfonic anhydride, or the like in the presence of a base such as Et₃N, iPr₂NEt, pyridine, 4-dimethylaminopyridine, or the like at a temperature of from −76° C. to 0° C. from 20 minutes to 2 hours, (affording IVa), followed by treatment with a brominating agent, such as lithium bromide, sodium bromide, tetraethylammonium bromide, tetra-n-butylammonium bromide, or the like in a solvent such as, dichloromethane, acetonitrile, tetrahydrofuran, dimethylformamide, or the like at a temperature of from 20° C. to 100° C. from 30 minutes to 5 hours, yields the resulting 4-bromo-4-deoxysugar V, which upon treatment with sodium cyanide, potassium cyanide (in the presence or absence of a crown ether), tetraethylammonium cyanide, tetra-n-butylammonium cyanide, tetraethylammonium chloride-sodium cyanide, or the like in a solvent such as dichloromethane, acetonitrile, tetrahydrofuran, dimethylformamide, dimethylsulfoxide, hexamethylphosphoramide, or the like at a temperature of from 30° C. to 150° C. from 15 minutes to 24 hours yields the desired material VI.

Intermediate IV can also be transformed into VI via the 4-chloro-4-deoxy- or 4-deoxy-4-iodo-tetradeoxy-D-lyxopyranosides, Va or and Vb, respectively, in a similar manner as that described for the 4-bromo-4-deoxy derivative V.

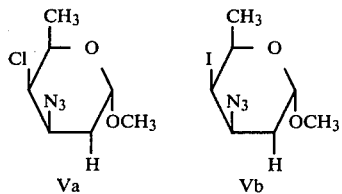

Va        Vb

Chloride Va can be obtained either directly from IV by treatment with sulfuryl chloride in a solvent such as dichloromethane, chloroform, diethyl ether, or the like, in the presence of a base such as pyridine, triethylamine, i-Pr2NEt, 4-dimethylaminopyridine, or the like, at a temperature of from −76° to 30° for from 1 to 24 hours, or indirectly by nucleophilic displacement of the trifluoromethanesulfonyloxy group in IVa with chloride anion, such as tetra-n-butyl ammonium chloride. Iodide Vb is obtained by nucleophilic displacement of the trifluoromethanesulfonyloxy group in IVa with iodide anion, such as sodium iodide, potassium iodide, tetraethylammonium iodide, tetra-n-butylammonium iodide, or the like. Displacement of the chloro group in Va or the iodo group in Vb with cyanide anion, as described with bromide V, yields VI.

The desired compound VI may also be prepared by the following scheme:

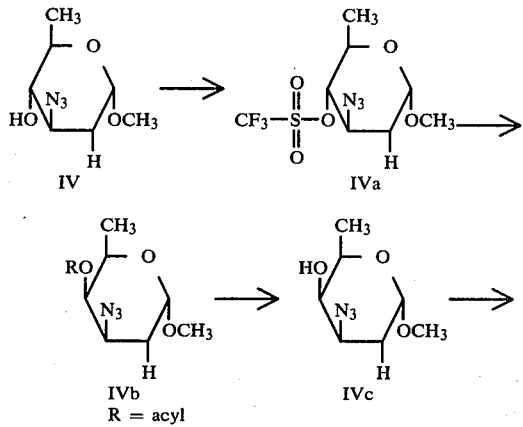

R = acyl

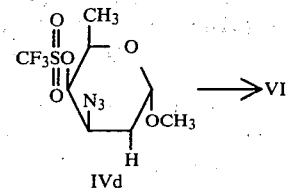

In words relative to the above reaction sequence, compound IV may be transformed into compound VI via intermediates IVa, IVb, IVc, and IVd. Preparation of IVa is already described in the process for compound V. Treatment of IVa with sodium acetate or benzoate, tetraethylammonium acetate or benzoate, tetra-n-butylammonium acetate or benzoate, or the like, in a solvent such as acetonitrile, dimethylformamide, dimethylsulfoxide, hexamethylphosphoramide, or the like at a temperature of from 30° to 180° C. for from 15 minutes to 48 hours yields acetate or benzoate IVb. De-esterification of IVb with methanolic sodium methoxide or the like affords methyl 3-azido-2,3,6-trideoxy-α-D-lyxohexopyranoside (IVc). Activation of IVc to afford IVd is carried out in like manner as that described for activation of IV into IVa, and conversion of IVd into VI by reaction with cyanide anion is performed in a similar fashion as that described for conversion of V into VI.

In the foregoing word description of the above reaction diagram for the synthesis of compound VI, it is to be understood that there is considerable latitude in selection of precise reaction parameters. Suggestion of this latitude and its breadth is generally indicated by enumeration of equivalent solvents system, temperature ranges, protecting groups and range of identities of involved reagents.

The following examples illustrate, but do not limit the product or process aspects of the present invention. All temperature expressions are in °C.

EXAMPLE 1

Process for preparing Methyl 3-azido-4-C-cyano-2,3,4,6-tetradeoxy-α-D-arabinohexopyranoside

STEP A

Methyl 2,6-dideoxy-3-O-(p-toluenesulfonyl)-α-D-arabinohexopyranoside

To a solution of methyl 2,6-dideoxy-α-D-arabinohexopyranoside (6.3 g, 38.8 mmol) in pyridine (200 ml) at 0° C. is added freshly recrystallized p-toluenesulfonyl chloride (7.6 g, 39.9 mmol). The mixture is kept 5 days at 0° C., at which time additional p-toluenesulfonyl chloride (1.9 g) is added. After 3 days at 5° C., the mixture is poured into ice-water, extracted several times with dichloromethane, the combined organic extracts evaporated under vacuum, coevaporated several times with toluene, and chromatographed on silica gel (Merck No. 7734) (1:2 diethyl ether-petroleum ether, b.p. 35+−60° C.) to yield 8.5 g (69%) of the product as a solid; $^1$H NMR (300 MHz, CDCl$_3$): δ1.30 (d, C-CH$_3$), 1.83 (td, H-2ax, J-H-1, H-2ax, 3.5 Hz, J H2eq, H2ax 12.8 Hz), 2.09 (m, H-2eq, J H-1, H-2eq 1.1 Hz, J H-2eq, H-3 5.5 Hz), 2.46 (s, ArCH$_3$), 2.53 (d, OH), 3.27 (s, OCH$_3$), 3.32 (td, H-4, $J_{H\text{-}4\text{-}H\text{-}5} = J_{H\text{-}4, H\text{-}3} = 8.8$ Hz), 3.65 (m, H-5), 4.68 (broad d, H-1), 4.74 (ddd, H-3), 7.38 (d, 2H, Ar), 7.85 ppm (d, 2H, Ar); mass spectrum m/e 285 (M—OCH$_3$), 272 (M—CH$_3$CHO).

Anal. C, H, S.

STEP B

Methyl 3-Azido-2,3,6-trideoxy-α-D-arabino-hexopyranoside

To a solution of methyl 2,6-dideoxy-3-O-(p-toluenesulfonyl)-α-D-arabino-hexopyranoside (8.4 g, 26.6 mmol) in absolute ethanol (80 ml) is added phenolphthalein (as an indicator) and subsequently dropwise at 60° C. saturated ethanolic sodium hydroxide until color persists for ~10 minutes. The reaction mixture is then cooled to 10° C., the precipitated sodium tosylate removed by filtration, the filtrate brought to pH 7 with 2 N hydrochloric acid. Sodium azide (4.9 g) and ammonium chloride (2.9 g) are then added, and the mixture is stirred overnight at reflux temperature. After concentration, the residue is partitioned between dichloromethane and water, the aqueous layer extracted with dichloromethane, the combined organic extracts evaporated under vacuum, and chromatographed on silica gel (Merck No. 7734) (30:1 chloroformethyl acetate) to afford the pure product as a colorless syrup; yield 3.7 g (74%); $^1$H NMR (300 MHz, CDCl$_3$): δ1.30 (d, C-CH$_3$), 1.73 (td, H-2ax, $J_{H-1,H-2ax}$ 3.6 Hz), 2.17 (m, H-2eq, $J_{H-1, H-2eq}$ 1.2 Hz, $J_{H-2eq, H-3}$ 5 Hz), 3.14 (t, H-4, $J_{-H-3, H-4}=J_{H-4, H-5}=9$ Hz), 3.34 (s, OCH$_3$), 3.63–3.79 (m, H-3,5), 4.75 (broad d, H-1); mass spectrum m/e 187 (M), 156 (M—OCH$_3$), 145 (M-N$_3$), 143 (M—CH$_3$CHO).

STEP C

Methyl 3-azido-4-bromo-2,3,4,6-tetradeoxy-α-D-lyxohexopyranoside

To a solution of methyl 3-azido-2,3,6-trideoxy-α-D-arabino-hexopyranoside (3.6 g, 19.2 mmol) in dichloromethane (100 ml) cooled in an ice-bath are added pyridine (2 ml) and dropwise a solution of trifluoromethanesulfonic anhydride (3.2 ml, 19.0 mmol) in dichloromethane (25 ml). After stirring for 10 minutes at 0° C. with exclusion of moisture, additional pyridine (2 ml) and trifluoromethanesulfonic anhydride (2.6 ml) are added. After 10 minutes at 0° C., the reaction mixture is diluted with dichloromethane (130 ml) and poured into a separatory funnel containing ice-water. The organic layer is separated and washed with cold N hydrochloric acid, saturated sodium hydrogencarbonate, water, and dried (sodium sulfate). Evaporation under vacuum gives the 4-trifluoromethanesulfonate that is dissolved in dry acetonitrile (50 ml) and treated with tetra-n-butylammonium bromide (12.7 g, 39.4 mmol) for 1 hour at 40° C. The reaction mixture is concentrated, the residue partitioned between dichloromethane and water, the organic layer evaporated under vacuum and the resulting syrup chromatographed on a column of silica gel (Merck No. 7734) (1:2 dichloromethane-hexane) to yield 3.65 g (76%) of the bromide; $^1$H NMR (300 MHz, CDCl$_3$): δ1.32 (d, C-CH$_3$), 1.90 (dd, H-2eq), 2.20 (td, H-2ax), 3.36 (s, OCH$_3$), 3.84–400 (m, H-3,5), 4.27 (d, H-4), 4.86 ppm (d, H-1); mass spectrum m/e 250 (M).

STEP D

Methyl 3-azido-4-C-cyano-2,3,4,6-tetradeoxy-α-D-arabino-hexopyranoside

To a solution of methyl 3-azido-4-bromo-2,3,4,6-tetradeoxy-α-D-lyxo-hexopyranoside (3.5 g, 14.0 mmol) in freshly distilled acetonitrile (75 ml) is added tetra-n-butylammonium cyanide (7.5 g, 28.0 mmol). The reaction mixture is stirred for 1 hour at 50° C., cooled, partially concentrated (~25 ml), diluted with dichloromethane (250 ml), washed with water (3X), dried (sodium sulfate), and evaporated under vacuum. The residue is chromatographed on a column of silica gel (Merck No. 7734) (1:10 diethyl ether-hexane) to yield 687 mg (25%) of the desired cyanide as a colorless syrup; $^1$H NMR (300 MHz, CDCl$_3$): δ1.42 (d, C-CH$_3$), 1.60 (td, H-2ax, $J_{H-1,H-2ax}$ 3.5 Hz), 2.21 (m, H-2eq, $J_{H-1, H-2eq}$ 1.2 Hz, $J_{H-2eq, H-3}$ 5 Hz), 2.26 (t, H-4, $J_{H-3, H-4}=J_{H-4,H-5}=10.8$ Hz), 3.36 (s, OCH$_3$), 3.92–4.06 (m, H-3,5), 4.85 (broad d, H-1); mass spectrum m/e 165 (M—OCH$_3$), 154 (M—N$_3$), 152 (M—CH$_3$CHO).

What is claimed is:

1. The compound having the structure:

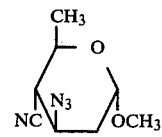

which is methyl 3-azido-4-C-cyano-2,3,4,6-tetradeoxy-α-D-arabino-hexopyranoside.

2. The compound:

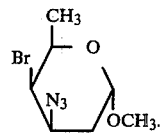

* * * * *